Figure 1:
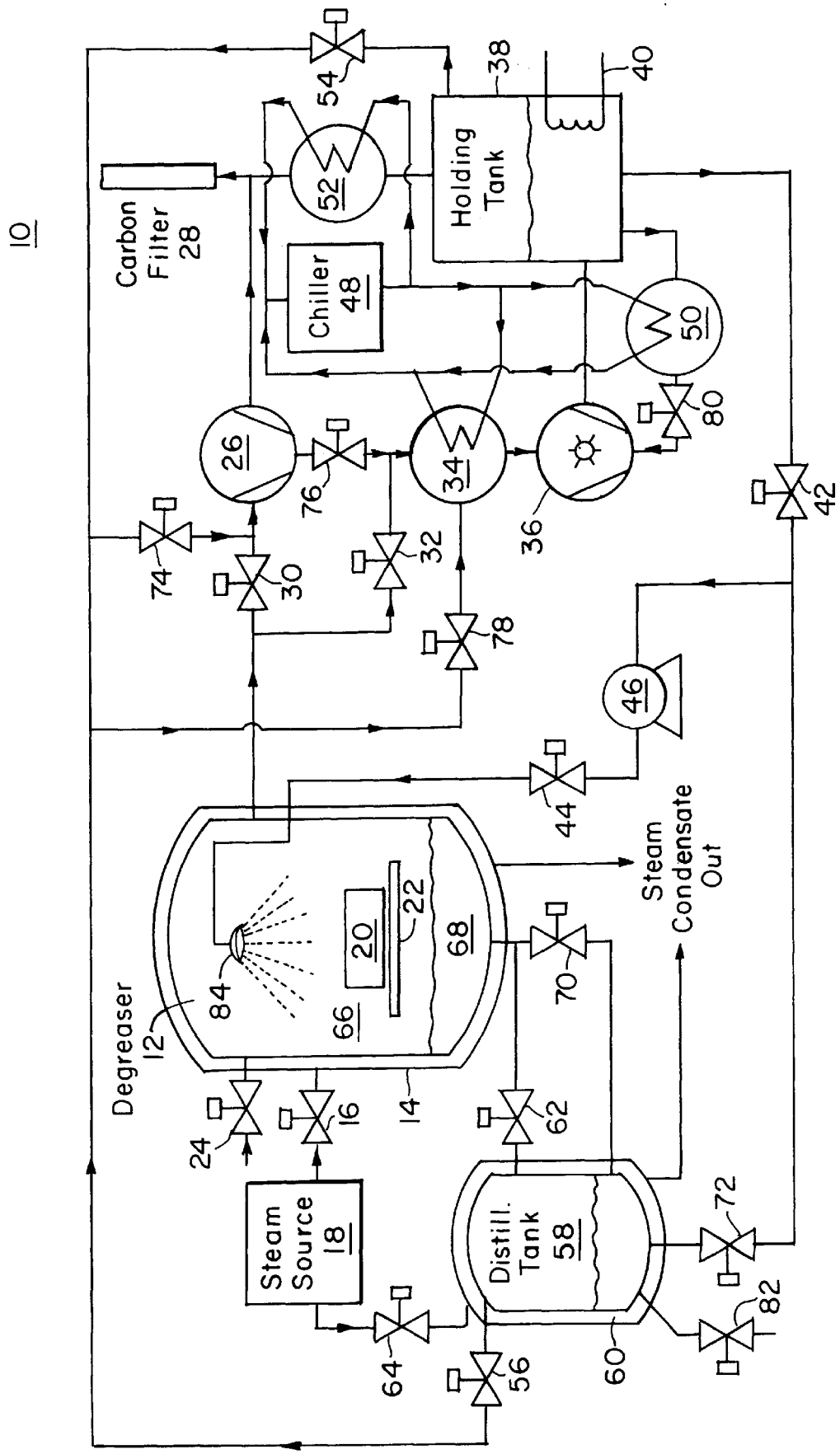

United States Patent

Gray et al.

[11] Patent Number: 6,004,403
[45] Date of Patent: Dec. 21, 1999

[54] SOLVENT CLEANING SYSTEM

[75] Inventors: Donald J. Gray, East Greenwich; Peter T. E. Gebhard, Providence, both of R.I.

[73] Assignee: Gebhard Gray Associates, Providence, R.I.

[21] Appl. No.: 08/648,258

[22] Filed: May 13, 1996

Related U.S. Application Data

[60] Division of application No. 08/281,303, Jul. 27, 1994, Pat. No. 5,538,025, which is a continuation-in-part of application No. 08/053,161, Apr. 26, 1993, Pat. No. 5,469,876, which is a division of application No. 07/787,935, Nov. 5, 1991, Pat. No. 5,240,507.

[51] Int. Cl.$^6$ ..................................................... B08B 3/10
[52] U.S. Cl. ............................... 134/10; 134/12; 68/18 R
[58] Field of Search ..................................... 68/18 R, 18 C, 68/18 F; 134/105, 108, 12, 11, 10; 8/158

[56] References Cited

U.S. PATENT DOCUMENTS

| | | |
|---|---|---|
| 3,388,567 | 6/1968 | Oles ........................................ 68/18 R |
| 3,610,260 | 10/1971 | Kearney . |
| 3,801,274 | 4/1974 | Gleason ................................... 68/18 C |
| 3,937,043 | 2/1976 | Hughes et al. ........................... 68/18 R |
| 4,459,831 | 7/1984 | Grandi ..................................... 68/18 R |
| 4,581,133 | 4/1986 | Tomes ..................................... 68/18 C |
| 4,637,232 | 1/1987 | Zucchini ................................. 68/18 C |
| 4,813,247 | 3/1989 | Takeda .................................... 68/18 C |
| 4,865,061 | 9/1989 | Fowler et al. . |
| 4,879,888 | 11/1989 | Suissa . |
| 4,984,318 | 1/1991 | Palau . |
| 5,056,174 | 10/1991 | Hagiwara . |
| 5,106,404 | 4/1992 | Grant . |

*Primary Examiner*—Frankie L. Stinson
*Attorney, Agent, or Firm*—Iandiorio & Teska

[57] ABSTRACT

A improved solvent cleaning method and system which is truly a closed system in which the object to be cleaned is placed in a chamber and subjected to a negative gauge pressure to remove air and other non-condensible gases after which a solvent is introduced to the evacuated chamber and the object is cleaned and then the solvent is recovered from the object and chamber within the closed system before the clean object is removed.

12 Claims, 2 Drawing Sheets

SOLVENT CLEANING SYSTEM

RELATED INVENTIONS

This is a division of application Ser. No. 08/281,303, filed Jul. 27, 1994 now U.S. Pat. No. 5,538,025.

Which is a continuation in part of application Ser. No. 08/053,161 filed Apr. 26, 1993 now U.S. Pat. No. 5,469,876 which is a divisional application of Ser. No. 07/1787,935 filed Nov. 5, 1991 issued as U.S. Pat. No. 5,240,507 on Aug. 31, 1993.

FIELD OF INVENTION

This invention relates to an improved cleaning system, and more particularly to a closed solvent cleaning method and system which virtually eliminates the mixture of the solvent with air throughout the cleaning operation. Eliminating air from the cleaning process and the solvent recovery and solvent cleaning process allows complete recovery of the vapors by conventional condensing thereby controlling emissions to the surroundings.

BACKGROUND OF INVENTION

Cleaning operations are becoming more and more of a burden on industry because of the ever-stricter environmental requirements for disposition of compounds used in the cleaning operations and resulting effluents. Cleaning operations effected include those involving clothing, rugs and furnishings, as well as those of a more industrial nature such as involving the cleaning and degreasing of metals, ceramics, plastics and other materials. Solvent cleaning processes, those using a solvent to degrease and clean, are the most prevalent. There are two types of solvent cleaning processes: open and closed. Open systems are still the most commonly used, but their appeal is shrinking with increasing demands of environmental safety. Open systems include such approaches as solvent vapor degreasing, solvent ultrasonic cleaning, cold or hot solvent dipped and solvent spray systems. These systems suffer from a number of shortcomings, among the most important of which are the contamination of the environment and the cost of constantly replenishing the non-recoverable solvent. In addition, the cost of equipment to contain the vapor and to properly dispose of the vapor and liquid waste is becoming more and more formidable.

The closed systems, so-called, attempt to combat these problems but with indifferent success. The loss of solvent as vapor and liquid still occurs, even in a so-called closed system because the vapor escapes when the cleaned parts are removed and the parts carry off solvent which clings to their surfaces and resides in the pores of the material. Further, attempts to recover the solvent are expensive and less than totally successful. For, even though the system is "closed" when the solvent is introduced to the closed chamber, it mixes with the air there. After the cleaning operation, the solvent in liquid form can be easily separated from the air, but not so with solvent in vapor form. That requires a major effort. Even if the air and solvent are condensed, only a small amount of solvent can be recovered.

Therefore, these systems are not truly closed. Incineration is one technique for getting rid of solvent but that requires significant investment in special equipment, it uses extra heat energy, and solvent is lost and must then be replenished. Steam stripping is a technique which actually recovers the solvent, but it too requires special equipment and heat energy to make the steam. In addition, the steam must be condensed to water and then separated from the solvent.

Thus, conventional cleaning systems have problems in the area of hazardous emissions and solvent recovery. They are generally limited to operating at specific temperatures and pressures. They typically do not dry all the solvent off the objects before exposing them to the atmosphere. They utilize heat energy during a substantial part, if not all, of the cleaning cycle. Conventional systems also need a great deal of solvent to fill their cleaning tanks and require additional energy input to pump the solvent through the system. In addition, standard solvent vapor cleaning systems must use solvents whose vapors are heavier than air. These vapors are confined in a blanket over the boiling solvent by using expensive refrigerator coils and by limiting the dimensions of the system tank. These systems operate at fixed temperatures which are determined by the boiling point of the solvent at atmospheric pressure.

A different approach, known as vacuum degreasing, avoids some of the problems of solvent cleaning. In this approach the contaminants are exposed to a high temperature, low-pressure environment in order to reach pressures below the vapor pressure of the contaminant. Essentially the contaminant is boiled off the parts. The problem here, however, is that some contaminants generally have a very low vapor pressure. Consequently, extremely high vacuums and/or temperatures are required. Although solvents are not emitted, the contaminant itself is often emitted which can become a problem. And, this process is generally costly due to the sub torr pressures and high temperatures required. In many cases, non-volatile residue, either present in the contaminant originally (i.e., sulfur residue) or residue resulting from a breakdown of the contaminant due to the high temperature requirements (e.g. carbon deposits) are often left behind on the parts. The pollution abatement energy costs and cleaning efficiency requirements strongly limit the applications of such a system.

SUMMARY OF INVENTION

It is therefore an object of this invention to provide an improved closed circuit solvent cleaning system and method.

It is a further object of this invention to provide such an improved closed circuit solvent cleaning system and method which employs the solvent in either vapor or liquid form or both.

It is a further object of this invention provide such an improved closed circuit solvent cleaning system and method which enables solvent recovery and limits hazardous emissions.

It is a further object of this invention provide such an improved closed circuit solvent cleaning system which is operative at various temperatures to accommodate different objects to be cleaned and different solvents.

It is a further object of this invention to provide such an improved closed circuit solvent cleaning system which is operative at various temperatures and pressures other than the boiling point at atmospheric pressure of the solvent used.

It is a further object of this invention provide such an improved closed circuit solvent cleaning system and method in which solvent is dried off the object before any venting to atmosphere occurs.

It is a further object of this invention to provide such an improved closed circuit solvent cleaning system and method which more efficiently cleans by condensation of vapor on parts causing a vapor wash and cleaning.

It is a further object of this invention provide such an improved closed circuit solvent cleaning system and method which is much more efficient because heat is required for much less of the time during the cycle.

It is a further object of this invention provide such an improved closed circuit solvent cleaning system and method which uses much less solvent.

It is a further object of this invention provide such an improved closed circuit solvent cleaning system and method which removes volatile contaminants prior to any exposure to solvent.

It is a further object of this invention provide such an improved closed circuit solvent cleaning system and method which employs internally generated differential pressures to drive the solvent through the system.

It is a further object of this invention provide such an improved closed circuit solvent cleaning system and method which is not restricted to operate with any particular solvent.

It is a further object of this invention provide such an improved closed circuit solvent cleaning system and method which virtually eliminates mixture of the solvent with air throughout the cleaning operation and therefore eliminates the difficult step of separating the solvent from the air after the cleaning operation is completed.

It is a further object of this invention to provide such an improved closed circuit solvent cleaning system and method which allows parts to be cleaned by solvent immersion or solvent spray, or both.

It is a further object of this invention to provide such an improved closed circuit solvent cleaning system and method which throttles solvent vapors about the parts to be cleaned thereby aiding in drying the parts after cleaning.

It is a further object of this invention to provide such an improved closed circuit solvent cleaning system which allows any contaminated solvent to also be cleaned, and cleaned within the closed circuit.

The invention results from the realization that an efficient, economical, safe, and environmentally sound solvent cleaning technique which is a truly closed operation can be effected, without the burden of having to separate the solvent from air after the cleaning operation, by evacuating a cleaning chamber containing parts to be cleaned before the solvent is introduced so that the solvent and air never meet, thus eliminating exposure to atmosphere. The airless solvent can then be easily extracted and condensed and even cleaned for reuse prior to the exposure of the chamber and parts to air during the removal of parts from the chamber after the cleaning operation has been completed.

This invention features and may suitably comprise, consist of, or consist essentially of a closed circuit solvent cleaning method comprising the steps of placing the object to be cleaned in a chamber and subjecting the chamber to a negative gauge pressure to remove air and other non-condensible gases. Following this, a solvent is introduced to the evacuated chamber and the object is cleaned. The solvent is then recovered from the object and chamber and the chamber is vented to atmosphere and the clean object is removed.

In a preferred embodiment the negative gauge pressure is in the range of atmospheric to zero atmospheric absolute. The solvent may be introduced in a vapor state or a liquid state, or both. The temperature of the chamber may be varied to control the temperature and vapor density of the solvent to increase or decrease the penetration of the solvent into the object to be cleaned and to create more or less pressure that can be used to drive the solvent through the closed system. Recovering the solvent includes withdrawing from the chamber the solvent in liquid state including the contaminants, and then drawing off from the chamber the solvent in the vapor state. Withdrawing the liquid solvent may include maintaining the chamber at an elevated temperature to generate increased pressure in the chamber and positively drive out the solvent in the liquid state with the contaminants. The drawing off of the solvent in the vapor state may include drying the object of solvent.

The invention also features an apparatus for accomplishing the technique of the invention including a closed solvent cleaning system. There is a chamber for holding an object to be cleaned and means for applying a negative gauge pressure to the chamber to remove air and other non-condensible gases. There are also means for introducing to the chamber the solvent for cleaning the object and means for recovering the solvent from the object and chamber. Storage means stores the recovered solvent.

In a preferred embodiment, the chamber may include a heat exchanger for varying the temperature of the chamber. The means for applying a negative gauge pressure may include a vacuum pump and the means for introducing the solvent may include a valve means associated with the storage means. The means for recovering may include a drain for extracting the solvent liquid and contaminants and may include means for extracting the solvent vapor as well. The storage means may include one reservoir for receiving the solvent vapor and a second reservoir for receiving the solvent liquid, and there may be means for condensing the solvent vapor.

The system may also include means for spraying solvent over the parts to be cleaned, for immersing the parts in solvent, or both. In addition, there may be means for throttling solvent vapors into the chamber to assist in drying parts. Means for processing and cleaning contaminated solvent within the closed circuit includes a distilling tank and a holding tank and means for heating the distillation tank, distilling solvent vapor and urging the distilled vapor into the holding tank.

DISCLOSURE OF PREFERRED EMBODIMENT

Figure 2:
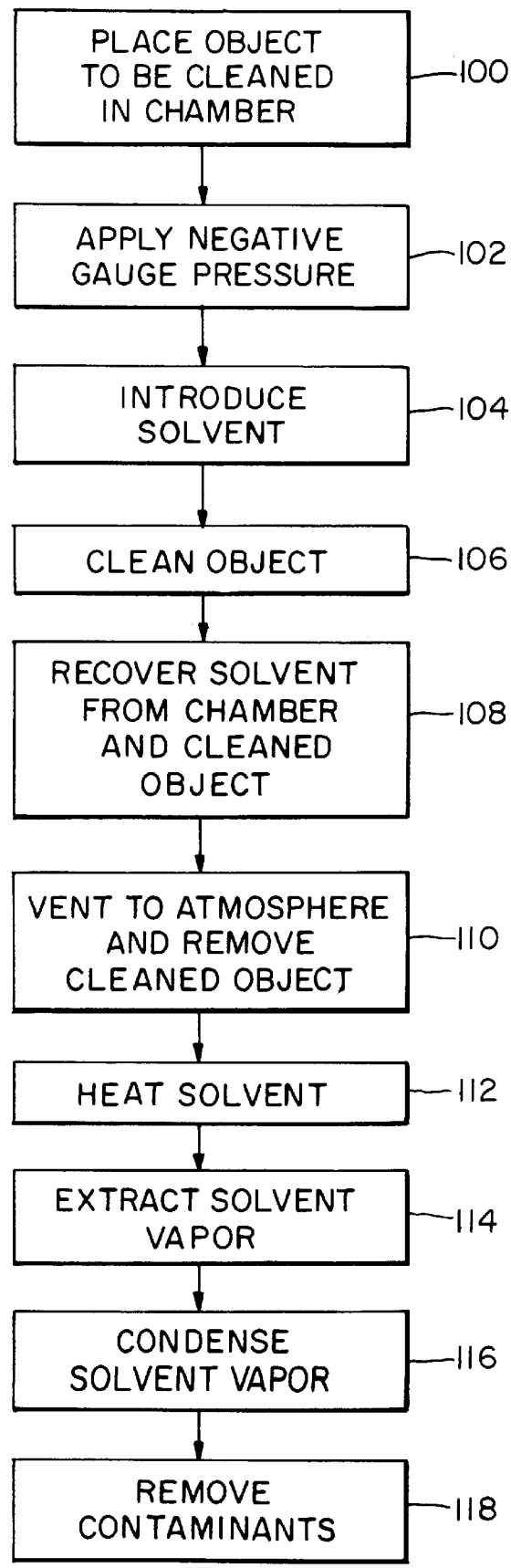

Other objects, features and advantages will occur to those skilled in the art from the following description of a preferred embodiment and the accompanying drawings, in which:

FIG. 1 is a schematic diagram of a closed circuit solvent cleaning system according to this invention; and FIG. 2 is a flow chart depicting the operation of the improved closed circuit solvent cleaning system of FIG. 1 according to this invention.

The invention may be accomplished in a closed circuit solvent cleaning technique in which the object to be cleaned is placed in a chamber, and then subjecting the chamber to a negative gauge pressure in order to remove the air and other non-condensible gases from the chamber. Solvent cleaning as used herein includes vapor degreasing, clothing dry cleaning,and solvent immersion washing. In conventional solvent cleaning systems, most of the problems with the loss of expensive solvent result from the fact that the solvent vapors become mixed with air. The air then is either vented, requiring expensive and complex equipment for preventing environmental contamination, or the air with the vapor is put through a recovery process which can be equally expensive and complex, in order to recover the expensive solvent and cleanse the air before it is vented to atmosphere. This invention results from the realization that the entire problem can be eliminated or at least dramatically reduced by not allowing the solvent vapors to become mixed with air at all: to prevent any mixing at any time of the solvent with the air. This is done by evacuating the chamber of air and other non-condensible gases before any solvent is introduced so that the chamber contains only the object to be cleaned. The chamber is evacuated by employing a negative pressure which generally is less than the vapor pressure at the present operating temperature of the solvent and the contaminants to be removed such as water vapor and non-condensible gases. Sub-torr levels are not generally required. Torr levels of 0–700 torr are preferred. Ranges of 10–500 torr are workable and levels of 100 torr or less have had good results. After the solvent has been introduced and the part cleaned, the solvent is then recovered from the chamber and the object before the chamber is opened and vented to the atmosphere. Thus there is no contaminated air and the solvent may be recovered easily without the necessity to separate it from air. Depending on operating temperature, typically a negative gauge pressure in the range of atmospheric to slightly above zero atmospheric absolute is sufficient.

With the chamber evacuated, it is typically at a lower pressure than the solvent, which is stored in a holding tank. The opening of a valve then permits the solvent to flow or to flash in vapor form from the higher to the lower pressure in the chamber without requiring pumping equipment and the added expense of the energy required. Liquid as well as vapor phase solvent can be introduced to the chamber at this point. Once the solvent has been introduced into the chamber, the object is cleaned. Cleaning can be accomplished by vapor or liquid immersion and/or by solvent spray in the chamber. Because of the control afforded by the closed operation of this invention, the solvent can be heated or cooled and/or the pressure can be increased or decreased to whatever levels are desirable for a particular cleaning task. For example, the pressure in the chamber can be increased above atmospheric to enhance cleaning efficiency or the temperature could be increased above the ambient temperature. Then before the object is removed or there is any venting to atmosphere, the solvent is returned to the storage tank and recovered. The liquid may be recovered first, as it typically will reside at the bottom of the tank and contain in it the contaminants that have been removed from the, clean part. This liquid solvent can be drained by gravity back to the holding tank or the temperature of the chamber can be increased to increase the pressure in the chamber so that the liquid solvent can be driven back to the holding tank.

Subsequent to this the vapor may be drawn off and fed back to a separate holding tank or a separate compartment of the original holding tank. Included in this step may be the introduction of solvent vapor, preferably by throttling the vapor though a valve to assist in drying parts and removing solvent from the parts prior to removing the parts from the chamber. Separation is desirable between the vapor recovery and the liquid recovery because the vapor in this case is effectively a distillation product and will remain quite clean compared to the liquid which contains the contaminants. The vapor may be condensed in its travel back to the holding tank. Following the removal of the solvent in all its phases, the chamber may be opened to atmosphere so that the parts can be removed. The vapor removal from the chamber is sufficiently thorough so that a drying of the parts occurs as well as the removal of the vapor from the chamber. A heat exchanger or similar device may be associated with the chamber in order to control the temperature of the cleaning process. Thus certain materials which cannot withstand elevated temperatures or perhaps even room temperatures during the cleaning process may be accommodated by simply cooling the chamber. The heat exchanger may also increase the temperature in the chamber to accomplish a number of different goals. Increased temperature increases the penetration of the vapor into the part to be cleaned and thus enhances the cleaning function. Increased temperature also increases the chemical and physical cleaning characteristics of the solvent and thus enhances the cleaning function. Increased temperature also increases the vapor pressure in the chamber which can be used to drive out the liquid and vapor solvents as indicated previously. The temperature or cooling that is applied to the chamber may be applied only during the cleaning cycle at a great saving of energy over those systems that have heat, for example, applied during the entire operation.

One of the advantages of such a system is that it can work with solvents in the vapor form, in the liquid form or both, and it can work with a variety of different solvents, e.g., 1.1.1. trichloroethane, trichloroethylene, methylene chloride, perchloroethylene, Freon, aldehydes, alcohols, amines, ketones, aromatics, or other solvents which may or may not be heavier than air. Another important feature of the system according to this invention is that it overcomes the problem of solvent and/or liquid penetrating small areas such as tapped holes in the parts to be cleaned. Since the air is removed before solvent is introduced to the part in the system of this.

Such a system enables solvent recovery, which is increasingly important as solvent prices increase, and also limits hazard emissions, which is equally important as the regulations for emissions become more stringent and the cost of abiding by those regulations becomes more expensive.

Added features of this invention are that it uses much less solvent since the vapor is flashed into the cleaning chamber with at worst only a small amount of liquid; that is, the entire cleaning chamber or tank does not have to be filled as is often the case with open circuit systems.

Another important advantage of the subject closed circuit system is that the initial evacuation of the chamber after the parts are inserted for cleaning but before the solvent has been introduced, operates to remove volatile contaminants that may be associated with the parts even before the solvent is introduced.

The system 10, FIG. 1 for implementing the technique of this invention includes a cleaning or degreasing tank or chamber 12, which includes a heat exchanger 14. Valve 16 controls the inlet flow of the heating or cooling fluid. In this specific embodiment it is a heating fluid obtained from steam source 18. Other options for heating chamber 12 include electrical heaters or other heat transfer liquids such as oil. A part to be cleaned 20 may be placed on a suitable support 22 within chamber 12. Valve 66 operates to vent chamber 52 to the atmosphere. Pump 26 is used to apply a negative gauge pressure to chamber 12 when it is operating as a vacuum pump. An activated charcoal filter may be added to absorb any residual solvent vapors before they enter the vacuum pump. Valve 30 operates to vent the outflow through vacuum pump 26 to carbon filter 28 while valve 32, in a different portion of the cycle, directs the outflow to condenser 34 through vacuum pump 36 to holding tank 38. Holding tank 38 provided with a heater 40 communicates through valves 42 and 44, respectively, that communicates through pump 46 with chamber 120.

Chiller unit 48 is used to provide coolant to heat exchangers 34, 50, and 52. Other conventional means for providing cooling include cold water directly from a source of cold water or from a cooling tower. Valves 54 and 56 are used to purge air from holding tank 38 and distillation tank 58 respectively, and deliver it to a carbon filter 28 or a similar filter before it is vented to atmosphere. A third input to carbon filter 28 may be delivered through valve 30 which may be interconnected with degreasing tank or chamber 12 so that the outflow from vacuum pump 26 upon the evacuation of chamber 12 can be filtered first through carbon filter 28 before it is vented to atmosphere. This is especially important if there are volatile toxic contaminants associated with the parts that can be drawn off by the initial evacuation of chamber 12.

In operation, with the solvent stored in distilling tank 58, heater 60 is activated to increase the temperature of the solvent such as tetrachloroethylene to 100° C., producing a 400 torr vapor pressure. Heating is accomplished by steam directed though valve 64 from steam source 18. Heating can be accomplished by other conventional means such as electric heaters or heat transfer fluids. Valve 24 is then opened, venting chamber 12 to atmosphere, part 20 is placed on support 22 in chamber 12, valve 24 is closed and vacuum pump 26 is operated. All of the air and non-condensible gases and any volatile contaminants are drawn off by vacuum pump 26 and are directed by open valve 30 directly to atmosphere or, alternatively, through and carbon filter 28, and then to atmosphere. Vacuum pump 26 is then shut off. Since the tetrachloroethylene solvent in distilling tank 58 is at 100° C., with a 400 torr vapor pressure, when valve 62 is opened, the vapor flashes into chamber 12 so that the vapor 66 fills chamber 12 and condenses on and cleans part 20. If desired, liquid solvent 68 may also be introduced by opening valve 70 and partially or fully filing chamber 12 to submerge part 20 for liquid cleaning. If spraying is desired, valves 44 and 42 are opened and pump 46 is operated to draw solvent through sprayer 84 in chamber 12 or valve 72 is opened to draw solvent from tank 72. Valves 16 and 64 may now be opened and steam source 18 is activated to increase the temperature of chamber 12 to approximately 121° C., providing a 760 torr or 1 atmosphere pressure in the chamber during cleaning. After the cleaning cycle has been completed, the steam source 18 may be shut down and valves 16 and 64 closed. Valve 62 may be periodically opened to allow the liquid solvent 68 to gravity drain back through open valve 62 to distilling tank 58. Or more typically, the increased pressure of 760 torr will drive the liquid with its contaminants back into the distilling tank 58. The pressure in chamber 12 now drops to about 400 torr.

Following this, vacuum pump 36 may be operated with heat exchanger 34 on and valve 32 open. This draws off the vapors 66 in tank 12 including the vapors associated with object 20 so that it is dried during this process. The vapor, being virtually pure, is condensed in condenser 34 and delivered back to holding tank 38, which stores only clean solvent which may be used when the solvent in distilling tank 58 becomes contaminated and must be removed and processed. Periodic purging of the air in tanks 38 and 56 is accomplished through valves 54 and 56. Drying of part 20 in chamber 12 may be assisted by throttling vapor solvent in tank 58 through valve 62 while simultaneously pulling vapor out of chamber 12 through valve 78 and condensor 34 by means of pump 36.

Finally, vacuum pump 34 is stopped and valve 24 is opened to vent chamber 12 to atmosphere and part 20 is removed, having been dried and cleaned without introducing any hazardous waste to the atmosphere. Simultaneously, the solvent has been fully recovered with a minimum of effort and expense since it was not mixed with air and there is no need to undertake the expensive an complex procedures required to separate solvent from air and clean the air of the solvent contaminants.

When the solvent in distilling tank 58 becomes contaminated, the solvent can be distilled by opening valve 64 from steam source 18, and flashing vapors through open valves 56 and 78. Pump 36 pulls vapors through condensor 34 and sends clean solvent into holding tank 38. Upon solvent recovery, contaminants can be removed from distillation tank 58 through valve 82. Clean solvent can then be returned to distilling tank 58 through valves 42 and 72 for reuse.

There is shown in FIG. 2 a flow chart depicting the operation of system 10, FIG. 1, of this invention. The object to be cleaned, such as a piece of clothing or a manufactured part, is placed in the cleaning chamber in step 100. Then a negative gauge pressure is applied in step 102. This removes air and other non-condensible gases and it also removes any volatile contaminants. The gasses evacuated from the chamber at this point can be passed through suitable filters if this is necessary. The negative gauge pressure is typically between atmospheric and zero atmospheric absolute. Pressures in the range of 10 torr appear to be sufficient. Following this, the solvent is introduced in step 104. This can be done in vapor or liquid form, or both. Then the object is cleaned, step 106, for an appropriate period of time. During this time, the temperature can be varied to favor the appropriate conditions for the material or object being cleaned and also to improve vapor density and penetration of the solvent into the object. The temperature increase or decrease is effected only during the cleaning operation so that there is a substantial saving in energy. There can also be a substantial saving in energy by the fact that an increased temperature of the chamber increases the differential pressure between the two chambers to the point where that differential pressure alone could be used to drive out the solvent after the cleaning operation is done. Typically, with the solvent being present partially as a liquid and partially as a vapor, the solvent is recovered in step 108 by first removing the liquid which contains the contaminants, and then removing the vapor which is virtually clean since it is a distillation product. A complete removal of the vapor at this point also effects a drying of the object, which further minimizes the contamination of the environment with solvents in vapor or liquid form that would ordinarily cling to the object. Finally, in step 34, the chamber is opened to atmosphere and the cleaned object is removed.

When the solvent becomes contaminated, it is distilled by first heating the solvent, step 112 and then extracting the solvent vapor step 114. The solvent vapor is condensed, step 176 and stored in a separate tank. The contaminates are then removed, step 118.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A closed circuit solvent cleaning method comprising:
   placing an object to be cleaned in a chamber sealable with respect to the atmosphere;
   applying a negative gauge pressure to the chamber to remove air and other non-condensable gases;
   introducing a solvent to the evacuated chamber;
   cleaning the object while maintaining an airless environment within chamber;

recovering the solvent from the object and chamber; and processing and cleaning contaminated solvent within the closed circuit.

2. The method of claim 1 in which introducing a solvent includes introducing solvent vapors into the chamber.

3. The method of claim 1 in which introducing a solvent includes introducing liquid solvent to at least partially fill said chamber.

4. The method of claim 1 in which introducing a solvent includes spraying solvent about the object to be cleaned.

5. The method of claim 1 in which introducing a solvent includes preheating the solvent before it is introduced into the chamber.

6. The method of claim 1 in which cleaning includes heating the chamber during cleaning.

7. The method of claim 1 in recovering the solvent from the object and the chamber includes urging liquid solvent in the chamber to flow into a distilling tank.

8. The method of claim 1 in which recovering the solvent from the object and the chamber includes drawing vapor from the chamber to a holding tank.

9. The method of claim 8 in which drawing vapor from the chamber to the holding tank further includes condensing the vapor before delivery to the holding tank.

10. The method of claim 1 in which processing and cleaning contaminated solvent includes heating and distilling the contaminated solvent.

11. The method of claim 10 in which processing and cleaning contaminated solvent includes distilling solvent vapor and urging the distilled vapor into a holding tank.

12. The method of claim 1 further including drying the part in the chamber by throttling vapor solvent into the chamber while simultaneously pulling vapor out of the chamber.

* * * * *